US006353020B1

(12) United States Patent
Young et al.

(10) Patent No.: US 6,353,020 B1
(45) Date of Patent: Mar. 5, 2002

(54) FUNGICIDAL COMPOSITIONS CONTAINING N-ACETONYLBENZAMIDES

(75) Inventors: David Hamilton Young, Ambler; Willie Joe Wilson, Chalfont; Anne Ritchie Egan; Enrique Luis Michelotti, both of Fort Washington, all of PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/615,462

(22) Filed: Jul. 13, 2000

Related U.S. Application Data

(63) Continuation-in-part of application No. 09/433,848, filed on Nov. 4, 1999, now Pat. No. 6,107,340, which is a continuation-in-part of application No. 09/148,522, filed on Sep. 4, 1998, now Pat. No. 6,011,065.
(60) Provisional application No. 60/072,673, filed on Jan. 27, 1998, now abandoned.

(51) Int. Cl.$^7$ ......................... A01N 43/08; A01N 37/18
(52) U.S. Cl. ....................................... 514/472; 514/617
(58) Field of Search .................................. 514/617, 472

(56) References Cited

U.S. PATENT DOCUMENTS

| | | | |
|---|---|---|---|
| 5,304,572 A | 4/1994 | Michelotti et al. | 514/514 |
| 5,677,333 A | 10/1997 | Loughner et al. | 514/491 |

OTHER PUBLICATIONS

Tomlin, The Pesticide Manual Incorporating The Agrochemicals Handbook, Tenth Edition, (1995), pp. 745 and 746.*

* cited by examiner

*Primary Examiner*—Allen Robinson
(74) *Attorney, Agent, or Firm*—Clark R. Carpenter

(57) ABSTRACT

The present invention relates to fungicidal compositions and their use as a method for controlling phytopathogenic fungi comprising the application of a selected fungicidally active N-acetonylbenzamide compound and a second fungicidally active compound selected from an acylalanine type fungicide to plant seed, to plant foliage or to a plant growth medium. The compositions and method of use provide higher fungicidal activity than separate use of the same compounds.

5 Claims, No Drawings

FUNGICIDAL COMPOSITIONS CONTAINING N-ACETONYLBENZAMIDES

This is a continuation-in-part application of Ser. No. 09/433,848 filed Nov. 4, 1999 now U.S. Pat. No. 6,107,340, which is a continuation-in-part of Ser. No. 09/148,522, filed Sep. 4, 1998 now U.S. Pat. No. 6,011,065, which claims for domestic priority Ser. No. 60/072,673 filed Jan. 27, 1998, now abandoned.

The present invention relates to new fungicidal compositions and their use as a method for controlling phytopathogenic fungi on plants.

It is always desirable to improve products which can be used by growers in order to combat fungal diseases of crops, and in particular diseases caused by fungi in the class Oomycetes.

It is also always desirable to reduce the doses of chemical products spread into the environment to combat fungal attacks on crops, in particular by reducing the application doses of the products.

It is also always desirable to increase the number of antifungal products available to growers in order that they will find, among these products, the one which is best suited to the grower's specific use.

One objective of the invention is thus to provide novel fungicidal compositions which are useful against the problems outlined above.

Another objective of the invention is to propose novel fungicidal compositions which are useful in the preventive and curative treatment of diseases caused by fungi of the class Oomycetes.

Still another objective of the invention is to propose novel fungicidal compositions which are of improved efficacy against mildew and/or late blight caused by Oomycetes.

Yet another objective of the invention is to propose novel fungicidal compositions which are of improved efficacy against downy mildew in grapes and other crops and/or late blight in tomatoes and potatoes.

It has now been found that these objectives may be achieved, partly or totally, by means of the fungicidal compositions according to the present invention.

U.S. Pat. Nos. 5,304,572 and 5,677,333 disclose applying mixtures of the N-acetonylbenzamides disclosed therein with other fungicidal compounds. It has now been discovered that application of the N-acetonylbenzamides disclosed in these patents in combination with selected other fungicidal compounds provides unexpectedly high fungicidal activity and is effective in controlling phytopathogenic fungi at lower N-acetonylbenzamide dosage rates than those disclosed in the U.S. Pat. No. 5,304,572. Although U.S. Pat. No. 5,677,333 discloses the use of N-acetonylbenzamides in combination with ethylene bisdithiocarbamates, cymoxanil and dimethomorph to provide unexpectedly high fungicidal activity, the synergistic combinations of this invention are not disclosed or suggested in that patent.

In a first embodiment of this invention, there is provided a composition comprising (a) a fungicidally effective amount of a first fungicidally active compound having the formula (I)

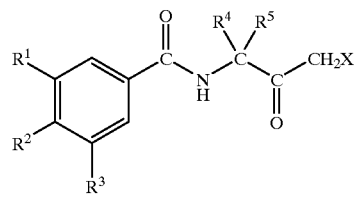

or an agronomically acceptable salt thereof
wherein
$R^1$ and $R^3$ are each independently halo or $(C_1-C_4)$alkyl,
$R^2$ is $(C_1-C_4)$alkyl, $(C_2-C_4)$alkenyl, $(C_2-C_6)$alkynyl, $(C_1-C_4)$alkoxy or cyano,
$R^4$ and $R^5$ are each independently a hydrogen atom or $(C_1-C_4)$alkyl, provided that at least one of $R^4$ and $R^5$ is $(C_2-C_4)$alkyl and
X is halo, thiocyano or isothiocyano;
(b) a fungicidally effective amount of a second fungicidally active compound which is an acylalanine type fungicide such as the R-enantiomer of metalaxyl, the racemic mixture of metalaxyl, oxadixyl, furalaxyl, benalaxyl, ofurace and cyprofuram; and
(c) an agronomically acceptable carrier.

In a second embodiment of this invention, there is provided a method for controlling phytopathogenic fungi on a plant comprising the application of (a) a fungicidally effective amount of a first fungicidally active compound having the formula (I)

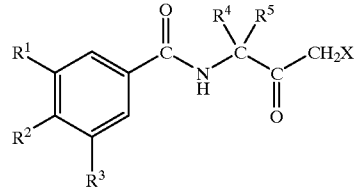

or an agronomically acceptable salt thereof
wherein
$R^1$ and $R^3$ are each independently halo or $(C_1-C_4)$alkyl,
$R^2$ is $(C_1-C_4)$alkyl, $(C_2-C_4)$alkenyl, $(C_2-C_6)$alkynyl, $(C_1-C_4)$alkoxy or cyano,
$R^4$ and $R^5$ are each independently a hydrogen atom or $(C_1-C_4)$alkyl, provided that at least one of $R^4$ and $R^5$ is $(C_2-C_4)$alkyl and
X is halo, thiocyano or isothiocyano;
(b) a fungicidally effective amount of a second fungicidally active compound which is an acylalanine type fungicide such as the R-enantiomer of metalaxyl, the racemic mixture of metalaxyl, oxadixyl, furalaxyl, benalaxyl, ofurace and cyprofuram; and
(c) an agronomically acceptable carrier to the plant seed, to the plant foliage or to the growth medium for the plant.

When $R^4$ and $R^5$ are different, optical enantiomers of the compounds of the present invention are possible due to the presence of an asymmetric carbon atom linking $R^4$ and R5. It is known that many biologically active compounds have optical enantiomers, one of which is more active than the other. Similarly, for compounds used in the method of the present invention, the biological activity of one enantiomer may exceed that of the other enantiomer, as described in EP 0 816 330 A1, Jan. 7, 1998.

"$(C_1-C_4)$alkyl" means a straight or branched alkyl group having one to four carbon atoms per group and includes methyl, ethyl, n-propyl, isopropyl, n-butyl, isobutyl, sec-butyl and tert-butyl.

"$(C_2-C_4)$alkenyl" means a straight or branched alkenyl group having two to four carbon atoms per group and includes, for example, ethenyl, 2-propenyl, 2-butenyl, 1-methylethenyl, 2-methyl-2-propenyl and the like.

"$(C_2-C_6)$alkynyl" means a straight or branched alkynyl group having from two to six carbons per group and includes, for example, ethynyl, 2-propynyl, 2-butynyl and the like.

"Halo" means chloro, fluoro, bromo and iodo.

"$(C_1-C_4)$alkoxy" means a straight or branched alkoxy group having one to four carbon atoms per group and includes, for example, methoxy, ethoxy, n-propoxy, isopropoxy, n-butoxy, isobutoxy, sec-butoxy and tert-butoxy.

"Cyano" means a group having the structural formula —CN.

"Thiocyano" means a group having the structural formula —SCN.

"Isothiocyano" means a group having the structural formula —NCS.

Agronomically acceptable salts include, for example, metal salts such as sodium, potassium, calcium and magnesium salts, ammonium salts such as isopropyl ammonium salts and trialkylsulfonium salts such as triethylsulfonium salts.

The first fungicidally active compound may be a single compound of formula (I) or, alternatively, may be a mixture of compounds of formula (I). Suitable compounds of formula (I) include, but are not limited to, N-[3'-(1'-chloro-3'-methyl-2'-oxopentan)]-3,5-dichloro-4-methylbenzamide,
N-[3'-(1'-chloro-3'-methyl-2'-oxopentan)]-3,5-dichloro-4-ethylbenzamide,
N-[3'-(1'-chloro-3'-methyl-2'-oxopentan)]-3,5-dichloro-4-ethoxybenzamide,
N-[3'-(1'-chloro-3'-methyl-2'-oxopentan)]-3,5-dichloro-4-methoxybenzamide,
N-[3'-(1'-chloro-3'-methyl-2'-oxopentan)]-3,5-dichloro-4-cyanobenzamide, and
N-[3'-(1'-chloro-3'-methyl-2'-oxopentan)]-3,5-dibromo-4-methylbenzamide.

In a preferred embodiment, the first fungicidally active compound is

N-[3'-(1'-chloro-3'-methyl-2'-oxopentan)]-3,5-dichloro-4-methylbenzamide,
N-[3'-(1'-chloro-3'-methyl-2'-oxopentan)]-3,5-dibromo-4-cyanobenzamide or a mixture thereof.

More preferably, the N-acetonyl benzamide compound is N-[3'-(1'-chloro-3'-methyl-2'-oxopentan)]-3,5-dichloro-4-methylbenzamide.

Suitable compounds which function as the second fungicidally active compound include, but are not limited to, the R-enantiomer of metalaxyl, the racemic mixture of metalaxyl, oxadixyl, furalaxyl, benalaxyl, ofurace and cyprofuram.

In a preferred embodiment, the second fungicidally active compound is selected from the group consisting of the R-enantiomer of metalaxyl, oxadixyl, ofurace and benalaxyl.

The method of the present invention may optionally further comprise application of other compounds having biological activity, for example, additional fungicidally active compounds or compounds having herbicidal activity or insecticidal activity, to the plant seed, to the plant foliage or to the growth medium for the plant.

The method of the present invention is useful for the control of phytopathogenic fungi on crops and the first and second fungicidally active compounds may be applied as a soil fungicide, as a seed protectant, as a foliar fungicide or as a combination thereof. In a preferred embodiment, the first and second fungicidally active compounds are applied to a plant growth medium, to the plant seed or to plant foliage at dosage rates of from 2 parts by weight (pbw) to 90 pbw, more preferably from 5 pbw to 75 pbw, of the first fungicidally active compound per 100 pbw of the combined amount of first and second fungicidally active compounds and from 10 pbw to 98 pbw, more preferably from 25 pbw to 95 pbw, of the second fungicidally active compound per 100 pbw of the combined amount of first and second fungicidally active compounds.

As a soil fungicide, the first and second fungicidally active compositions can be incorporated in the soil or applied to the surface of the soil at a dosage rate of about 0.25 kg to 5 kg of the first fungicidally active compound and from 0.25 kg to 5 kg of the second fungicidally active compound per hectare.

As a seed protectant, the first and second fungicidally active compounds are coated on seed at a dosage rate of about 0.5 kilograms (kg) to 5 kg of the first fungicidally active compound and from 0.5 kg to 5 kg of the second fungicidally active compound per 100 kg seed.

As a foliar fungicide, the first and second fungicidally active compounds are applied to plant foliage at a dosage rate of from 0.01 kg per hectare to 5 kg per hectare of the first fungicidally active compound, and a dosage rate of from 0.01 kg per hectare to about 5 kg per hectare of the second fungicidally active compound. In a preferred embodiment, the first fungicidally active compound is applied to plant foliage at a dosage rate of from 0.05 kg per hectare to about 0.5 kg per hectare. In a preferred embodiment, the second fungicidally active compound is applied to plant foliage at a dosage rate of 0.05 kg per hectare to 2.0 kg per hectare. The first and second fungicidally active compounds can be applied to plant foliage as fungicidal sprays by methods commonly employed, such as conventional high-gallonage hydraulic sprays, low-gallonage sprays, air-blast, aerial sprays and dusts. While the dilution and rate of application will depend upon the type of equipment employed, the method and frequency of application desired and diseases to be controlled, the effective amount is typically from about 0.1 kg to about 5 kg, preferably 0.2 kg to 2.5 kg, of both the first and second active compounds per hectare.

The first and second fungicidally active compounds may be applied simultaneously or sequentially.

In a preferred embodiment, the first and second fungicidally active compounds are simultaneously applied to plant growth medium, the plant seed, plant foliage or a combination thereof as a composition comprising a mixture of the first fungicidally active compound and second fungicidally active compound. In the preferred embodiments, the mixture includes from 2 pbw to 90 pbw of a first fungicidally active compound and from 10 pbw to 98 pbw of a second fungicidally active compound per 100 pbw of the mixture.

In an alternative embodiment, the first and second fungicidally active compounds are applied sequentially to the plant seed, plant foliage or plant growth medium, with application of the second-applied compound following application of the first-applied compound by up to 72 hours. The compounds may be applied in either order: either the first fungicidally active compound followed by the second fungicidally active compound or, alternatively, as application of the second fungicidally active compound followed by the first fungicidally active compound.

The method of the present invention is useful in controlling certain phytopathogenic fungi, particularly fungi of the class Oomycetes, and provides high fungicidal activity and relatively low phytotoxicity. The method of the present invention is particularly effective in controlling Oomycete fungi of the genera Phytophthora, Plasmopara, Peronospora, Albugo and Pseudoperonospora, and even more particularly against the organisms of those genera that cause diseases such as late blight in tomatoes and potatoes and downy mildew in grapes, cucumbers and other crops, including, for example, *Phytophthora infestans, Plasmopara viticola* and *Pseudoperonospora cubensis*.

For each of the above disclosed purposes, the first and second fungicidally active compounds can be used in the technical or pure form as prepared, as solutions or as formulations. The compounds are usually taken up in a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated. It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's "Emulsifiers and Detergents", McCutcheon's "Emulsifiers and Detergents/Functional Materials" and McCutcheon's "Functional Materials" all published annually by McCutcheon Division of MC Publishing Company (New Jersey).

In general, the compositions utilized in this invention can be dissolved in appropriate solvents such as acetone, methanol, ethanol, dimethylformamide or dimethyl sulfoxide and such solutions extended with water. The concentrations of the combined first and second active compounds in the solution can vary from 1% to 90% with a preferred range being 5% to 50%.

For the preparation of emulsifiable concentrates, the compositions used in the invention can be dissolved in suitable organic solvents or a mixture of solvents, together with an emulsifying agent which permits dispersion of the first and second active compounds in water. The concentration of the combined first and second active compounds in emulsifiable concentrates is usually 10% to 90% and in flowable emulsion concentrates, this can be as high as 75%. Wettable powders suitable for spraying, can be prepared by admixing the composition with a finely divided solid, such as clays, inorganic silicates and carbonates, and silicas and incorporating wetting agents, sticking agents, and/or dispersing agents in such mixtures. The concentration of the combined first and second active compounds in such formulations is usually in the range of 20% to 98%, preferably 40% to 75%.

Dusts are prepared by mixing the composition of the present invention, or salts and complexes thereof, with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the combined first and second active compounds are commonly made and are subsequently diluted to 1% to 10% use concentration.

The method of the present invention, wherein an N-acetonylbenzamide and a selected second fungicidally active compound are applied to plant seed, plant foliage or to a plant growth medium, unexpectedly provides higher fungicidal activity than the same compounds used separately.

The results provided by the mixtures were compared with the predicted results that were calculated using the formula set forth by S. R. Colby in Weeds 1967, 15, 20–22 ("Colby's Formula") from the results obtained using each of the compounds individually. The predicted results are also provided in the following examples and tables. This examples, tables and experimental procedure are provided for guidance to the practitioner and are not meant to limit the scope of the invention which is defined by the claims.

EXAMPLE 1a

In vitro Test to Control *Phytophthora capsici* Using N-[3'-(1'-chloro-3'-methyl-2'-oxopentan)]-3,5-dichloro-4-methylbenzamide (Compound A) and the R-Enantiomer of Metalaxyl (Compound B)

Dilution series of Compounds A and B were prepared in dimethylsulfoxide (DMSO), and aliquots added to 25 ml of molten potato dextrose agar at 50° C. to give the appropriate concentrations shown in the table below. Immediately after adding the compound(s), the molten agar was poured into 9-cm diameter petri plates and allowed to harden. The final concentration of DMSO in all plates was 0.5%. Control plates contained DMSO but neither compound. Plates were inoculated in the center with 1 µl of a suspension of *Phytophthora capsici* (ATCC 15399, obtainable from the American Type Culture Collection, Rockville, Md., U.S.A) zoospores containing $5 \times 10^5$ zoospores per milliliter. Three replicate plates were used for each treatment. Fungal colony diameters were measured after growth for 7 days at 25° C., and two measurements were taken from each plate. Inhibition of growth was calculated by comparing growth in the treatments with compound A and/or B with growth in the controls. Degree of inhibition (observed) is expressed as a percentage in Table 1a. The predicted % inhibition in treatments containing both A and B was calculated using the Colby Formula.

TABLE 1a

| Control of *Phytophthora capsici* | | | |
|---|---|---|---|
| Compound A Concentration ppm | Compound B Concentration ppm | % Inhibition (Observed) | % Inhibition (Predicted) |
| 0 | 0.25 | 17.9 | |
| 0 | 0.5 | 56.0 | |
| 0 | 0.75 | 57.6 | |
| 0.1 | 0 | 29.0 | |
| 0.1 | 0.25 | 52.2 | 41.7 |
| 0.1 | 0.5 | 76.1 | 68.8 |
| 0.1 | 0.75 | 82.0 | 69.9 |

EXAMPLE 1b

In vitro Test to Control *Phytophthora capsici* Using N-[3'-(1'-chloro-3'-methyl-2'-oxopentan)]-3,5-dichloro-4-methylbenzamide (Compound A) and the racemic mixture of Metalaxyl (Compound B')

Dilution series of Compounds A and B' were prepared in dimethylsulfoxide (DMSO), and aliquots added to 25 ml of molten potato dextrose agar at 50° C. to give the appropriate concentrations shown in the table below. Immediately after adding the compound(s), the molten agar was poured into 9-cm diameter petri plates and allowed to harden. The final concentration of DMSO in all plates was 0.5%. Control plates contained DMSO but neither compound. Plates were inoculated in the center with 1 μl of a suspension of *Phytophthora capsici* (ATCC 15399, obtainable from the American Type Culture Collection, Rockville, Md., U.S.A) zoospores containing 5×10$^5$ zoospores per milliliter. Three replicate plates were used for each treatment. Fungal colony diameters were measured after growth for 7 days at 25° C., and two measurements were taken from each plate. Inhibition of growth was calculated by comparing growth in the treatments with compound A and/or B' with growth in the controls. Degree of inhibition (Observed) is expressed as a percentage in Table 1b. The predicted % inhibition in treatments containing both A and B' was calculated using the Colby Formula, which is known to those skilled in the art (R. S. Colby, *Weeds* 15, 20–22 (1967)).

TABLE 1b

Control of *Phytophthora capsici*

| Compound A Concentration ppm | Compound B' Concentration ppm | % Inhibition (Observed) | % Inhibition (Predicted) |
|---|---|---|---|
| 0 | 0.6 | 35.1 | |
| 0 | 0.9 | 48.0 | |
| 0.04 | 0 | 31.0 | |
| 0.08 | 0 | 47.2 | |
| 0.12 | 0 | 52.3 | |
| 0.16 | 0 | 55.2 | |
| 0.04 | 0.6 | 59.3 | 55.2 |
| 0.08 | 0.6 | 76.1 | 65.7 |
| 0.12 | 0.6 | 84.5 | 69.0 |
| 0.16 | 0.6 | 100.0 | 70.9 |
| 0.04 | 0.9 | 90.0 | 64.1 |
| 0.08 | 0.9 | 78.70 | 72.5 |
| 0.12 | 0.9 | 100.0 | 75.2 |
| 0.16 | 0.9 | 100.0 | 76.7 |

EXAMPLE 2

In vitro Test to Control *Phytophthora capsici* Using N-[3'-(1'-chloro-3'-methyl-2'-oxopentan)]-3,5-dichloro-4-methylbenzamide (Compound A) and Oxadixyl (Compound C)

The experimental procedure and analysis were as described in Example 1a and the results presented in Table 2.

TABLE 2

Control of *Phytophthora capsici*

| Compound A Concentration ppm | Compound C Concentration ppm | % Inhibition (Observed) | % Inhibition (Predicted) |
|---|---|---|---|
| 0 | 6.25 | 30.3 | |
| 0 | 12.5 | 41.3 | |
| 0 | 25 | 50.8 | |
| 0.1 | 0 | 30.3 | |
| 0.1 | 6.25 | 68.9 | 51.4 |
| 0.1 | 12.5 | 71.3 | 59.1 |
| 0.1 | 25 | 95.2 | 65.7 |
| 0.2 | 0 | 39.3 | |
| 0.2 | 6.25 | 83.6 | 57.7 |

TABLE 2-continued

Control of *Phytophthora capsici*

| Compound A Concentration ppm | Compound C Concentration ppm | % Inhibition (Observed) | % Inhibition (Predicted) |
|---|---|---|---|
| 0.2 | 12.5 | 94.5 | 64.4 |
| 0.2 | 25 | 90.8 | 70.1 |
| 0.3 | 0 | 51.8 | |
| 0.3 | 6.25 | 100.0 | 66.4 |
| 0.3 | 12.5 | 100.0 | 71.7 |
| 0.3 | 25 | 96.6 | 76.3 |

EXAMPLE 3

In vitro Test to Control *Phytophthora capsici* Using N-[3'-chloro-3'-methyl-2'-oxopentan)]-3,5-dichloro-4-methylbenzamide Compound A) and Ofurace (Compound D)

The experimental procedure and analysis were as described in Example 1a results presented in Table 3.

TABLE 3

Control of *Phytophthora capsici*

| Compound A Concentration ppm | Compound D Concentration ppm | % Inhibition (Observed) | % Inhibition (Predicted) |
|---|---|---|---|
| 0 | 12.5 | 52.1 | |
| 0 | 25 | 56.0 | |
| 0.1 | 0 | 29.0 | |
| 0.1 | 12.5 | 93.8 | 66.0 |
| 0.1 | 25 | 93.8 | 68.8 |
| 0.2 | 0 | 38.1 | |
| 0.2 | 12.5 | 89.1 | 70.3 |
| 0.2 | 25 | 100.0 | 72.8 |
| 0.3 | 0 | 47.4 | |
| 0.3 | 12.5 | 91.8 | 74.8 |
| 0.3 | 25 | 100.0 | 76.9 |

EXAMPLE 4

In vitro Test to Control *Phytophthora capsici* Using N-[3'-(1'-chloro-3'-methyl-2'-oxopentan)]-3,5-dichloro-4-methylbenzamide (Compound A) and Benalaxyl (Compound E)

The experimental procedure and analysis were as described in Example 1a and the results presented in Table 4.

TABLE 4

Control of *Phytophthora capsici*

| Compound A Concentration ppm | Compound E Concentration ppm | % Inhibition (Observed) | % Inhibition (Predicted) |
|---|---|---|---|
| 0 | 20 | 46.6 | |
| 0.1 | 0 | 34.7 | |
| 0.1 | 20 | 97.6 | 65.1 |
| 0.2 | 0 | 44.5 | |
| 0.2 | 20 | 100.0 | 70.4 |
| 0.3 | 0 | 49.4 | |
| 0.3 | 20 | 99.3 | 73.0 |

We claim:

1. A fungicidal composition comprising synergistic fungicidally effective amounts of
   (a) a first fungicidally active compound which is N-[3'-(1'-chloro-3'-methyl-2'-oxopentan)]-3,5-dichloro-4-methylbenzamide,
   (b) a second fungicidally active compound compound which is ofurace, and
   (c) an agronomically acceptable carrier.

2. A method for controlling phytopathogenic fungi on a plant comprising the application of a synergistic fungicidally effective amount of the composition of claim 1.

3. The method of claim 2 wherein the phytopathogenic fungi belong to the class Oomycetes and are of the genera Phytophthora, Plasmopara, Peronospora, Albugo or Pseudoperonospora.

4. The method of claim 2 wherein the plant is a potato plant, a tomato plant, a grape plant or a cucumber plant.

5. The method of claim 2 wherein the amounts of the first and second fungicidally active compounds applied comprise from 2 parts by weight to 90 parts by weight of the first fungicidally active compound and from 10 parts by weight to 98 parts by weight of the second fungicidally active compound per 100 parts by weight of the combined amount of the first and second fungicidally active compounds.

* * * * *